United States Patent [19]

Smiley

[11] Patent Number: 4,906,783

[45] Date of Patent: Mar. 6, 1990

[54] PREPARATION OF BIS(HEXAMETHYLENE)TRIAMINE

[75] Inventor: Robert A. Smiley, Wilmington, Del.

[73] Assignee: E. I. Du Pont de Nemours and Company, Wilmington, Del.

[21] Appl. No.: 160,209

[22] Filed: Feb. 25, 1988

[51] Int. Cl.$^4$ ............................................. C07C 63/33
[52] U.S. Cl. ...................................... 564/492; 558/456
[58] Field of Search ........................ 564/492; 558/456

[56] References Cited

U.S. PATENT DOCUMENTS

| | | | |
|---|---|---|---|
| 2,257,814 | 10/1941 | Rigby | 564/492 |
| 3,950,229 | 4/1976 | Moore et al. | 558/456 |
| 3,972,938 | 8/1976 | Voges et al. | 564/492 |
| 4,115,304 | 9/1978 | Chadwick | 564/492 |
| 4,389,348 | 6/1983 | Diamond et al. | 564/492 |
| 4,601,859 | 7/1986 | Galle et al. | 564/492 |

*Primary Examiner*—Richard L. Raymond
*Assistant Examiner*—Raymond Covington

[57] ABSTRACT

Preparation of bis(hexamethylene)triamine from 6-aminohexanenitrile by catalytically preparing di(5-cyanopenyl)-amine, followed by hydrogenation using a nitride hydrogenation catalyst.

3 Claims, No Drawings

PREPARATION OF BIS(HEXAMETHYLENE)TRIAMINE

FIELD OF THE INVENTION

This invention relates to a process for the preparation of bis(hexamethylene)triamine, hereinafter sometimes referred to as "BHMT", from 6-aminohexanenitrile. BHMT has the chemical structure:

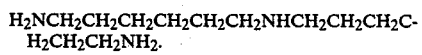

BACKGROUND OF THE INVENTION

BHMT is a byproduct from the manufacture of hexamethylenediamine. Large quantities of hexamethylenediamine are manufactured for use in the production of 6,6-nylon. It is conventional to separate the hexamethylenediamine from other reaction products by distillation. The distillation residue, still heels, contains varying amounts of BHMT, depending on how the plant is running. According to U.S. Pat. No. 4,115,304 to Chadwick, the distillation residue from one hexamethylenediamine plant contained the following amounts of the listed components:

| | |
|---|---|
| bis(hexamethylene)triamine | 5 to 40% by wt |
| C-10 diamine (primarily 1,4-di(aminomethyl)-1-ethyl cyclohexane) | 10 to 35% by wt |
| hexamethylene diamine and adiponitrile | 2 to 10% by wt |
| poly(hexamethylene)-polyamines and unknown compounds | 30 to 75% by wt |
| water | trace |
| ammonia | trace |

BHMT has been reported to have been recovered from such a residue by distillation: see U.S. Pat. No. 3,523,973 to Evans. However, because the BHMT has a high boiling point, attempts to separate it by distillation often lead to degradation and tar formation.

BHMT is useful as an additive in the manufacture of 6,6-nylon. It acts as a "branching agent", and according to U.S. Pat. No. 4,596,742 to Selivansky et al., in a sheath-core nylon yarn, wherein the sheath contains BHMT, the yarn has higher crimp development.

BHMT is also useful as an additive in 6,6-nylon polymers as a dye-receptor, can be added to asphalt to improve the bonding of the gravel to the other components, can be used in paper products, i.e., paper toweling, where it can replace diethylene triamine which acts to improve the wet strength of the paper products.

A process for the preparation of triamine by the reaction (deammoniation) of aliphatic diamines having 7 to 14 carbon atoms is disclosed in EPO Patent Application No. 0,212,287 published Mar. 4, 1987.

DESCRIPTION OF THE INVENTION

The present invention provides a process for the preparation of BHMT from 6-aminohexanenitrile. The process includes two separate chemical reactions which are set forth below:

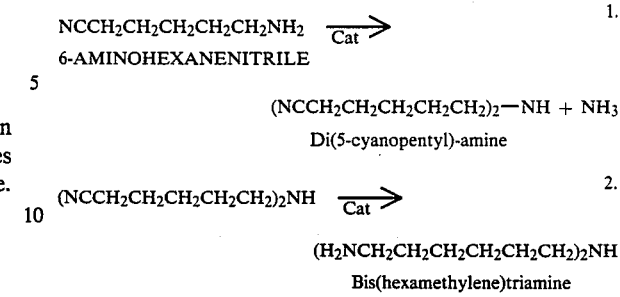

The first reaction is carried out in the presence of a catalyst containing at least one metal selected from the class consisting of palladium, platinum, rhodium and ruthenium. The amount of catalyst employed is not critical and will usually vary depending on whether the catalyst is supported or unsupported from about 0.25 g to 2 g per 100 grams of 6-aminohexanenitrile feed. The catalyst may be supported on alumina, silica, silica-alumina, carbon, or an inorganic salt such as barium carbonate or barium sulfate.

The first reaction is carried out at a temperature in the range of 50° C. to 250° C., perferably about 140° C. to 200° C. It is usually desirable to obtain about a 25 to 50% conversion. The reaction rate is temperature dependent, and at the preferred temperature range such a conversion will often take 10 to 20 hours.

The first reaction may be run at atmospheric pressure, but higher or lower pressure may be employed, for example, 0.1 to 5 atmosphere. Lower pressure will enhance the removal of ammonia. Bubbling an inert gas such as nitrogen through the reaction is beneficial.

The reaction product may be separated from the catalyst by filtration, or the reaction product decanted.

The starting material, 6-aminohexanenitrile, is a byproduct of the manufacture of hexamethylenediamine from adiponitrile. It can also be made deliberately by the partial hydrogeneration of adiponitrile.

The first reaction could be run in a solvent for the 6-aminohexanenitrile, but it is preferred to operate without a solvent.

In the second reaction, the product from the first reaction is hydrogenated using a nitrile hydrogenation catalyst. Such catalysts include, Raney cobalt, Raney nickel, supported cobalt, supported nickel, and iron oxide. In a preferred embodiment the catalyst contains a promoter such a as chromium. Such catalysts are commercially available, and contain about 0.5 to 6% by weight chromium. The catalyst can be used in a fixed bed system or a slurry system.

The second reaction can be carried out at a temperature in the range of about 75° to 200° C., preferably 110° to 150° C., and at a hydrogen pressure of about 300 to 5000 psig.

The second reaction can be carried out in a solvent such as alcohol or ethers, but the reaction is preferably carried out in the absence of solvent.

The final product, BHMT, may be separated from the reaction mixture by distillation.

The hydrogenation may be conducted continuously over a fixed-bed catalyst system or it can be run batch-wise whereby the catalyst is in a finely-divided state and mixed with the 6-aminonitrile to form a slurry. In the batch-wise state, the catalyst concentration can be varied from 0.5 to 20% by weight of the 6-aminonitrile charged with a preferred range of 5 to 15%. The rate of hydrogenation will depend on the catalyst concentration.

EXAMPLE

A charge of 452 g of 6-aminohexanenitrile was slurried with 10 g 5% palladium on alumina catalyst and heated to 150° C. for 12 hrs. while a slow stream of nitrogen was bubbled through the mixture. Analysis by gas chromatography showed a conversion to di(5-cyanopentyl)-amine of 26%. The reaction mixture was then hydrogenated for 6 hrs. to 600 psig $H_2$ over 28 grams of chromium-promoted Raney cobalt. (Such catalysts are described in W. R. Grace EPO Patent Application No. 0,212,986). The hydrogenated product contained 29% bis(hexamethylene)triamine by gas chromatographic analysis along with hexamethylendiamine and a small amount of hexamethyleneimine. The BHMT was isolated by distillation in almost 100% yield based on the 6-aminohexanenitrile conversion to dimer.

I claim:

1. A process for the preparation of bis(hexamethylene)triamine which comprises
   (a) reacting 6-aminohexanenitrile at a temperature of 50° to 250° C. in the presence of a catalyst containing at least one metal selected from the class consisting of palladium, platinum, rhodium, rhodium and ruthenium, for a reaction time of 10 to 20 hours at a reaction pressure in the range of 0.1 to 5 atmospheres,
   (b) separating the reaction products containing di-(5-cyanopentyl)amine from the catalyst,
   (c) hydrogenating the reaction products at a temperature of 75° to 200° C. at a hydrogen pressure 300 to 5000 psig in the presence of a hydrogenation catalyst selected from the class consisting of Raney cobalt, Raney nickel, supported cobalt, supported nickel and iron oxide, and
   (d) separating bis(hexamethylene)triamine from the reaction mixture.

2. The process of claim 1 in which the reaction products of step (a) are separated from the catalyst by decantation.

3. The process of claim 1 in which the bis(hexamethylene)triamine is separated from the reaction mixture by distillation.

* * * * *